US00PP09050P

United States Patent [19]

Henny

[11] Patent Number: Plant 9,050

[45] Date of Patent: Jan. 31, 1995

[54] DIEFFENBACHIA NAMED 695-1

[75] Inventor: Richard J. Henny, Tavares, Fla.

[73] Assignee: Florida Foundation Seed Producers, Inc., Greenwood, Fla.

[21] Appl. No.: 152,029

[22] Filed: Nov. 15, 1993

[51] Int. Cl.[6] ..... A01H 5/00

[52] U.S. Cl. ..... Plt./88.2

[58] Field of Search ..... Plt. 88.2

[56] References Cited

U.S. PATENT DOCUMENTS

P.P. 4504 2/1980 Welker ..... Plt. 88.2

P.P. 6402 11/1988 Stutzman ..... Plt. 88.2

*Primary Examiner*—James R. Feyrer

[57] ABSTRACT

A Dieffenbachia having distinctive variegated foliage having three colors on the upper leaf surface, with blotches and spots in light green areas of the leaves, white petiole color and a freely suckering habit provides a compact appearance.

1 Drawing Sheet

This invention relates to Dieffenbachia and in particular to a new cultivar which is the product of an intensive breeding program, the breeding program carried on in the vicinity of Apopka, Fla.

Among the many varieties which were used in the program are 'Lemon Sequine', 'Wilson's Delight', 'Perfection', and 'Perfection Compacta', with other unidentified varieties, none of which is patented so far as I can determine.

The basic objective of the program has been to produce an attractive commercial plant which provides an unusual variegated appearances, distinguishable from other variegated varieties.

As a result of crossing and re-crossing certain of the named varieties and in turn crossing and recrossing the results. I have reduced the basic crosses to certain numbered plants which appear in my records, including those identified as 64702, 64304, and 64710, with Compacta.

These crosses resulted in the parent varieties 68313 and 66508 when crossed produced the desired plant which I identify as 695-1, to be known as Dieffenbachia 695-1.

I have caused the plant hereof to be repeatedly propagated asexually by tissue culture near Apopka, Fla. and find that it has demonstrated the stability of characteristics which are described herein, in successive generations.

The various observations, measurements and values describe the Dieffenbachia 695-1 as it has been grown near Apopka, Fla., under greenhouse conditions which closely approximate those generally used in horticultural practice.

The new plant of this disclosure is readily distinguished from known plants of the same market class by the unique combination of characteristics including:

An unusually short internode spacing causing specimens to be very compact and have a high density of leaves to plant height, even with advancing specimen age.

Leaf petioles have long, wide wings of stipulate character, substantially only the tops and edges of which are deep green; the tops being lobed and the wings extend substantially the entire length of the petioles. The petioles are imbricated to an unusually high degree around the main stem of the plant, giving the plant the appearance of having a very wide, striated or ribbed stem. Wing lobes are foliaceous.

Leaves have unusually smooth margins that lack undulations to an unusual degree and have finer, less conspicuous leaf veining or ribs. The midribs are more nearly lacking green and form a straight, near-white line separating the two halves of leaf laminas.

Leaves of specimens of market size have a predominantly light green centerfield color which has random splotches of deep green spotting of characteristically random shapes and sizes over a light green to yellow predominant color. The leaves have narrow, continuous deep green margins, and a solid stripe, essentially white. There is apparently no chlorophyll, over the midrib of each leaf. The leaves have a resulting mottled, paisley appearance. The leaf coloration is further unusual in that the color patterns of the leaves do not follow the patterns of the veins but the white line is substantially always present.

The traits set forth hereinafter have been observed repeatedly and found to be basic characters of my plant 695-1 and serve to distinguish my plant from other Dieffenbachia of the same general type such as D. 'Camille' and D. 'Compacta' or in fact any of those described by Bailey or Graf, none of these being patented as far as I am aware.

The parent plants 68313 and 66508, proprietary breeding material, have been destroyed to conserve greenhouse space and were not released in commerce.

Attractive and distinct variegated foliage consisting of three colors on the upper leaf surface.

Dark green margins as well as blotches and spots within the light green areas of the leaves.

Leaf midrib is white and surrounded by a light green central area which occupies 40% to 50% of the leaf surface.

Petiole color is white and accents the leaf coloration.

Freely suckering habit gives the plant a compact and full appearance.

A typical plant of my new cultivar is shown in the drawing attached hereto, with color notations stated as measured against The Royal Horticultural Society Colour Chart.

As to be expected the colors are as nearly like those and as can be reproduced photographically depending on light level and fertilization rate among other elements.

Classification: Dieffenbachia × c.v. 695-1.

Propagation: Asexual production either by tissue culture or cuttings.

Plant: In a 15 cm standard pot, after approximately 22 weeks of growth under appropriate conditions beginning with a 10-week-old rooted liner obtained from tissue culture, 695-1 will be approximately 17–20 cm from the soil surface to the junction of the petioles of the most recently unfurled leaf, and approximately 24 to 30 cm in width. Plant height, with the leaves held upward, will be approximately 26–30 cm. The ultimate size of 695-1, if planted in a sufficiently large container and grown under appropriate conditions, is unknown. Stem: The stem color is 145D but is generally not visible due to the clasping nature of the petiole wings which surround the stem.

Petiole: The petiole color is 157A (green-white).

As before suggested the internode length appears to be unusually short for plants of this class. Internode length does not increase with progressive growth as with most hybrid Dieffenbachia plants. This plant remains compact with advancing maturity and has a higher canopy density than normal due to closely spaced internodes. This is an important characteristic from a commercial standpoint because it indicates longer periods between required transplantings of the specimens and/or reduced requirements for specimen renewal as plants grow too tall for their locality even though these plants do not grow very tall.

The leaves of this plant appear to be longer, narrower, more planar and smoother than normal for plants of this taxonomic class.

The primary ribs or veins of the leaves of this plant are not very deeply or greatly depressed.

Leaf: The leaf is ovate/lanceolate, with a acuminate apex and a cordate base which will sometimes be slightly oblique. The margin is entire. The lamina on either side of the midrib tends to be of slightly unequal widths, resulting in a slight curving of the blade towards the narrower side. The leaf blade, once fully expanded, is typically oriented 90 degrees to the stem.

*Dimensions.*—For the growing time and pot size indicated, the largest leaves will be approximately 10 cm × 22 cm whereas an average leaf will be 9 cm × 20 cm. Plant height, measured with the leaves held upright, will average 36 cm and plant spread from the leaf tips will be approximately 42 cm.

*Midrib.*—The midrib color is 157A (green-white) and tapers toward the apex. It protrudes prominently from the abaxial side of the leaf.

*Primary veins.*—The primary veins are sunken into the adaxial side and stand out from the abaxial side of the leaf blade. The color of the primary veins is the same as that of the adjacent leaf blade.

*Color and pattern.*—The adaxial side of the mature older leaf has a midrib color of 147A at the junction of the petiole abruptly changing to 145D for the length of the midrib ending 1.5 cm to 2 cm from the leaf apex. The background color of the leaf is 145C to 145A with blotches of 137A to 139A irregularly paralleling the primary veins. The margins are also 137A to 139A. The abaxial surface of the mature color leaf is 145A with the blotches from the adaxial surface showing through as 137C.

Axillary breaks: The plant branches freely, producing up to 15 or more lateral offshoots per main stem.

Blooming habit: Mature plants have been observed to flower in the spring in the greenhouse in Apopka, Fla.

The flowering of this plant does not differ noticeably from that of other commercial Dieffenbachia varieties.

The color variegations of this plant are also expressed in the spath and spadix formed.

Roots: Thick white roots with fine laterals.

I claim:

1. A new and distinct variety of Dieffenbachia plant substantially as described and shown herein, characterized particularly as to novelty by its variegated foliage, having three colors on the upper leaf surface, the dark green margins, blotches and spots in the light green areas of the leaves, the white midrib surrounded by light green central area over 40 to 50 percent of the leaf surface, the white petiole and freely suckering habit.

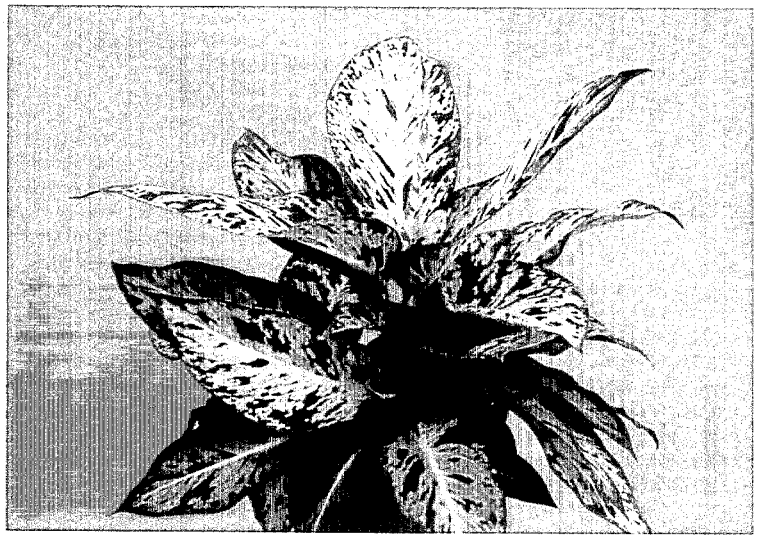

* * * * *